(12) United States Patent
Schuele et al.

(10) Patent No.: US 9,833,358 B2
(45) Date of Patent: Dec. 5, 2017

(54) METHOD AND SYSTEM FOR MODIFYING EYE TISSUE AND INTRAOCULAR LENSES

(75) Inventors: Georg Schuele, Menlo Park, CA (US); Dan Andersen, Menlo Park, CA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 84 days.

(21) Appl. No.: 12/987,069

(22) Filed: Jan. 7, 2011

(65) Prior Publication Data
US 2011/0172649 A1 Jul. 14, 2011

Related U.S. Application Data

(60) Provisional application No. 61/293,357, filed on Jan. 8, 2010.

(51) Int. Cl.
*A61F 9/008* (2006.01)

(52) U.S. Cl.
CPC .......... *A61F 9/008* (2013.01); *A61F 9/00827* (2013.01); *A61F 9/00812* (2013.01); *A61F 9/00834* (2013.01); *A61F 2009/0087* (2013.01); *A61F 2009/00842* (2013.01); *A61F 2009/00853* (2013.01); *A61F 2009/00872* (2013.01); *A61F 2009/00889* (2013.01)

(58) Field of Classification Search
CPC ........................................ A61F 9/008–9/009
USPC ....................................................... 606/4–7
See application file for complete search history.

(56) References Cited

U.S. PATENT DOCUMENTS

| | | |
|---|---|---|
| 4,784,135 A | 11/1988 | Blum et al. |
| 5,720,894 A | 2/1998 | Neev et al. |
| 5,957,915 A | 9/1999 | Trost |
| 5,984,916 A * | 11/1999 | Lai .................................. 606/11 |
| 6,019,472 A | 2/2000 | Koester et al. |
| 6,454,761 B1 | 9/2002 | Freedman |
| 6,596,966 B1 | 7/2003 | Kickelhain et al. |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |

(Continued)

FOREIGN PATENT DOCUMENTS

| | | |
|---|---|---|
| DE | 19855623 C1 | 2/2000 |
| DE | 102006036800 A1 | 2/2008 |

(Continued)

OTHER PUBLICATIONS

Lee et al. (Optical detection of intracellular cavitation during selective laser targeting of the retinal pigment epithelium: dependence of cell death mechanism on pulse duration. J. Biomed. Opt. (2007);12(6):064034).*

(Continued)

*Primary Examiner* — Nathan J Jenness
(74) *Attorney, Agent, or Firm* — Abbott Medical Optics Inc.

(57) ABSTRACT

As shown in the drawings for purposes of illustration, a method and system for making physical modifications to intraocular targets is disclosed. In varying embodiments, the method and system disclosed herein provide many advantages over the current standard of care. Specifically, linear absorption facilitated photodecomposition and linear absorption facilitated plasma generation to modify intraocular tissues and synthetic intraocular lenses.

15 Claims, 11 Drawing Sheets

(56) References Cited

U.S. PATENT DOCUMENTS

| | | |
|---|---|---|
| 8,382,745 B2 | 2/2013 | Naranjo-Tackman et al. |
| 8,414,564 B2 | 4/2013 | Goldshleger et al. |
| 2004/0049174 A1 | 3/2004 | Peyman |
| 2004/0102765 A1* | 5/2004 | Koenig .................. A61F 9/007 606/5 |
| 2006/0195076 A1* | 8/2006 | Blumenkranz ..... A61F 9/00736 606/4 |
| 2008/0177256 A1* | 7/2008 | Loesel et al. ...................... 606/4 |
| 2009/0161827 A1* | 6/2009 | Gertner .................. A61F 9/008 378/65 |
| 2009/0281620 A1 | 11/2009 | Sacharoff et al. |
| 2009/0318906 A1 | 12/2009 | Konig et al. |
| 2010/0163540 A1 | 7/2010 | Vogel et al. |
| 2010/0191230 A1* | 7/2010 | Dick et al. ......................... 606/5 |
| 2011/0028957 A1* | 2/2011 | Raksi et al. ....................... 606/6 |
| 2011/0098692 A1* | 4/2011 | Shazly .................. A61F 9/008 606/10 |
| 2011/0118712 A1* | 5/2011 | Lubatschowski et al. ........ 606/5 |
| 2011/0319873 A1 | 12/2011 | Raksi et al. |
| 2011/0319875 A1 | 12/2011 | Loesel et al. |

FOREIGN PATENT DOCUMENTS

| | | | |
|---|---|---|---|
| DE | 102007028042 B3 | 8/2008 | |
| DE | 102008005053 | * 7/2009 | ............. A61F 9/008 |
| EP | 1252872 A1 | 10/2002 | |
| EP | 1787607 A1 | 5/2007 | |
| WO | 2007/057174 A1 | 5/2007 | |
| WO | 2007084602 A2 | 7/2007 | |
| WO | WO 2008017428 A2 * | 2/2008 | |
| WO | 2008055506 A2 | 5/2008 | |
| WO | 2009003107 A1 | 12/2008 | |

OTHER PUBLICATIONS

J. Colombelli et al., "Ultraviolet Diffraction Limited Nanosurgery of Live Biological Tissues", Review of Scientific Instruments, American Institute of Physics, Feb. 2004, vol. 75 No. 2, pp. 472 to 478 (7 pages).

PCT International Search Report and Written Opinion for US/PCT2011/020610, Applicant Optimedica Corporation, Forms PCT/ISA/210, 220, and 237, dated May 3, 2011 (11 pages).

Julian Colombelli et al., "Ultraviolet diffraction limited nanosurgery of live biological tissues," Review of Scientific Instruments, vol. 75, No. 2, Feb. 2004, pp. 472-478, Copyright 2004 American Institute of Physics (7 pages).

Li Ding et al., Intratissue Refractive Index Shaping (IRIS) of the Cornea and Lens Using a Low-Pulse-Energy Femtosecond Laser Oscillator, Investigative Ophthalmology & Visual Science, Dec. 2008, vol. 49, No. 12, Copyright Associate for Research in Vision and Ophthalmology, pp. 5332-5339 (8 pages).

Extended European Search Report for Application No. EP14164301.5, mailed on Aug. 12, 2014, 8 pages.

* cited by examiner

METHOD AND SYSTEM FOR MODIFYING EYE TISSUE AND INTRAOCULAR LENSES

RELATED APPLICATION DATA

The present application claims the benefit under 35 U.S.C. §119 to U.S. provisional patent application Ser. No. 61/293,357, filed Jan. 8, 2010. The foregoing application is hereby incorporated by reference into the present application in its entirety.

BACKGROUND OF THE INVENTION

Cataract extraction is one of the most commonly performed surgical procedures in the world. A cataract is the opacification of the crystalline lens or its envelope—the lens capsule—of the eye. It varies in degree from slight to complete opacity that obstructs the passage of light. Early in the development of age-related cataract the power of the lens may be increased, causing near-sightedness (myopia), and the gradual yellowing and opacification of the lens may reduce the perception of blue colors as those wavelengths are absorbed and scattered within the crystalline lens. Cataract typically progresses slowly to cause vision loss and are potentially blinding if untreated. Treatment is performed by removing the opaque crystalline lens and replacing it with an artificial intraocular lens (IOL). An estimated 3 million cases are presently performed annually in the United States and 15 million worldwide. This market is composed of various segments including intraocular lenses for implantation, viscoelastic polymers to facilitate surgical maneuvers, disposable instrumentation including ultrasonic phacoemulsification tips, tubing, and various knives and forceps.

Modern cataract surgery is typically performed using a technique termed phacoemulsification in which an ultrasonic tip with associated irrigation and aspiration ports is used to sculpt the relatively hard nucleus of the lens to facilitate it removal through an opening made in the anterior lens capsule termed anterior capsulotomy or more recently continuous curvilinear capsulorhexis (CCC). Finally, a synthetic foldable intraocular lens is inserted into the remaining lens capsule of the eye through a small incision.

One of the most technically challenging and critical steps in the procedure is making the capsulorhexis. This step evolved from an earlier technique termed can-opener capsulotomy in which a sharp needle was used to perforate the anterior lens capsule in a circular fashion followed by the removal of a circular fragment of lens capsule typically in the range of 5-8 mm in diameter. This facilitated the next step of nuclear sculpting by phacoemulsification. Due to a variety of complications associated with the initial can-opener technique, attempts were made by leading experts in the field to develop a better technique for removal of the anterior lens capsule preceding the emulsification step.

The concept of the continuous curvilinear capsulorhexis is to provide a smooth continuous circular opening through which not only the phacoemulsification of the nucleus can be performed safely and easily, but also for easy insertion of the intraocular lens. It provides both a clear central access for insertion, a permanent aperture for transmission of the image to the retina by the patient, and also a support of the IOL inside the remaining capsule that would limit the potential for dislocation.

Problems may develop related to inability of the surgeon to adequately visualize the capsule due to lack of red reflex, to grasp it with sufficient security, to tear a smooth circular opening of the appropriate size and in the correct location without creating radial rips and extensions. Also present are technical difficulties related to maintenance of the anterior chamber depth after initial opening, small size of the pupil, or the absence of a red reflex due to the lens opacity. Some of the problems with visualization have been minimized through the use of dyes such as methylene blue or indocyanine green. Additional complications arise in patients with weak zonules (typically older patients) and very young children that have very soft and elastic capsules, which are very difficult to controllably and reliably rupture and tear.

Many cataract patients have astigmatic visual errors. Astigmatism can occur when the corneal curvature is unequal in all directions. Nowadays IOLs are used to correct for astigmatism but require precise rotational and central placement. Additionally, IOLs are not used for correction beyond 5D of astigmatism, even many patients have more severe abberations. Higher correction beyond 5D requires to reshape the cornea to become more spherical. There have been numerous approaches, including Corneaplasty, Astigmatic Keratotomy, Corneal Relaxing incision (CRI) and Limbal Relaxing Incision (LRI). Except the Corneaplasty all procedures are done by placing corneal incisions in a well defined manner and depth to allow the cornea to change shape to become more spherical. Nowadays these delicate cuts are placed manually with its implication on its limited precision.

But not only cuts are desired for ophthalmic therapies. There is also the need for more gentle modifications of the eye tissue which result in weakening of the tissues mechanical properties and or changes of the optical properties of the treated tissue. In this case the effect should be gentle enough to allow structural modifications of the eye tissue without mechanical disruption. Ding et al. (IOVS, 2008 (49), 12, pp 5532-5539) showed modification of corneal tissue with sub-rupture femtosecond laser pulses and could demonstrate changes in the refractive index by about 1% by applying diffraction patterns into the corneal tissue. The practical application of Ding's technique is although limited by the need to apply 100,000,000 laser pulses per cubic micrometer of treated tissue.

Vogel et al. (US 2010/0163540 A1) describes a method for machining and cutting of transparent material with temporal smooth laser beams to generate a low density plasma without the formation of plasma luminescence. In the teaching they describes that linear absorption of the exposed material is especially to be avoided as it leads to the random generation of seeding electrons which in turn generates a stochastic variation in the plasma threshold. Additionally they describe that the low density plasma formation is always associated with the formation of cavitation bubbles.

This is in strong contrast to the presented invention in which two working regimens are described. It was discovered that using a laser wavelength that has some linear absorption in the target tissue enables to create extremely low threshold effect. Additionally a temporal smooth pulse shape is not required in the current invention. Also the formation of a cavitation bubble is not desired in one embodiment of the invention as the effect is induced by linear absorption enhanced photodecomposition. Also Vogel's data show that there is still more than one order difference in achieving plasma formation when comparing IR femtosecond lasers and 355 sub-ns laser. In our embodiment, due to the use of the linear absorption of tissue intrinsic chromophores (or via the addition of exogenous chromophores) the energy threshold for the 355 nm sub-nanosecond laser is even slightly lower when compared to femtosecond laser pulses using the same numerical aperture optics.

Braun et al. (DE 198 55 623 C1) describes a method for precise machining inside of glass using a laser with wavelength outside the transmission plateau of the glass. This laser is then used to specifically create material defects inside the glass without comprising the surface. This method allows them to place material defects closer to the surface without damaging the surface itself. No surface effects are described. It also does not create any cavitation event as its used only on glass in which no cavitation bubble is formed.

Koenig et al. (WO 2007/057174) claims a system for the surgical intervention of the eye by using femtosecond laser pulses in the UV spectral range. In his teaching he describes the use of higher numerical apertures of 0.8 for his invention which lowers the threshold significantly into the nanoJoule regimen. But his makes the transfer of this system into a useable product so difficult as its optically difficult to have these numerical apertures combined with a wide scan ranges of 6 to 10 mm typically used for ophthalmic applications. Also the generation of femtosecond UV laser pulses is technically challenging.

What is needed are methods, techniques and an apparatus to advance the standard of care of the ophthalmic patient.

SUMMARY OF THE INVENTION

One embodiment is directed to a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds; and an optical system operatively coupled to the laser source and configured to focus and direct the laser beam in a pattern into one or more intraocular targets within an eye of a patient, such that interaction between the one or more targets and the laser pulses is characterized by linear absorption enhanced photodecomposition without formation of a plasma or associated cavitation event. The wavelength may be about 355 nm. The pulse duration may be between about 400 picoseconds and about 700 picoseconds. The pulses may have a pulse energy between about 0.01 microJoules and about 500 microJoules. The pulses may have a pulse energy of between about 0.5 microJoules and about 10 microJoules. The plurality of laser pulses may have a repetition rate of between about 500 Hertz and about 500 kiloHertz. The optical system may be configured to focus the laser beam to create a beam diameter of between about 0.5 microns and about 10 microns within the one or more intraocular targets. At least one of the one or more intraocular targets may be selected from the group consisting of a cornea, a limbus, a sclera, a lens capsule, a crystalline lens, and a synthetic intraocular lens implant. The pattern may be configured to create one or more physical modifications, such as cuts (incisions) and refractive index changes, in the intraocular target in a configuration selected from the group consisting of corneal relaxing incisions, limbal relaxing incisions, astigmatic keratotomies, and capsulotomies. The optical system and laser source may be configured to structurally alter at least one of the one or more intraocular targets such that an index of refraction of the altered tissue structure target is changed.

Another embodiment is directed to a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds; and an optical system operatively coupled to the laser source and configured to focus and direct the laser beam in a pattern into one or more tissue structure targets within an eye of a patient, such that interaction between the one or more targets and the laser pulses is characterized by localized formation of a plasma that is facilitated by linear absorption. The wavelength may be about 355 nm. The pulse duration may be between about 400 picoseconds and about 700 picoseconds. The pulses may have a pulse energy between about 0.01 microJoules and about 500 microJoules. The pulses may have a pulse energy of between about 0.5 microJoules and about 10 microJoules. The plurality of laser pulses may have a repetition rate of between about 500 Hertz and about 500 kiloHertz. The optical system may be configured to focus the laser beam to create a beam diameter of between about 0.5 microns and about 10 microns within the one or more tissue structure targets. At least one of the one or more tissue structure targets may be selected from the group consisting of a cornea, a limbus, a sclera, a lens capsule, a crystalline lens, and a synthetic intraocular lens implant. The pattern may be configured to create one or more cuts in the intraocular target that is tissue structure target in a configuration selected from the group consisting of corneal relaxing incisions, limbal relaxing incisions, astigmatic keratotomies, and capsulotomies.

Another embodiment is directed to a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds; and an optical system operatively coupled to the laser source and configured to focus and direct the laser beam in a pattern into one or more targets within an eye of a patient, such that interaction between the one or more targets and the laser pulses is characterized by linear absorption enhanced photodecomposition without formation of a plasma or associated cavitation event. The pattern may be configured such that the operation of the optical system and laser source causes physical alteration of the one or more targets. The physical alteration may be manifested as a change in refractive index of the one or more targets or one or more incisions. At least one of the one or more targets may be a cornea or an artificial intraocular lens. The physical alteration may be configured to change the refractive profile of the target.

Another embodiment is directed to a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds; an optical system operatively coupled to the laser source and configured to focus and direct the laser beam in a pattern into one or more tissue structure targets within an eye of a patient, such that interaction between the one or more targets and the laser pulses is characterized by linear absorption enhanced photodecomposition without formation of a plasma or associated cavitation event; and an integrated imaging susbsystem that captures in a confocal arrangement backreflected light from a sample provided by the laser source. The laser pulses may induce fluorescence that is collected by the imaging subsystem. The system may be configured to provide interleaved lower energy pulses for imaging and higher energy pulses for treatment. The imaging subsystem may comprise an optical coherence tomography system, a Purkinje imaging system, and/or a Scheimpflug imaging system. The system may further comprise a controller configured to determine the locations & shapes of ocular structures, to determine pattern placement and/or laser parameters, and position the patterns within the defined targets.

Another embodiment is directed to a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds; an optical system operatively coupled to the laser source and configured to focus and direct the laser beam in a pattern into one or more tissue structure targets within an eye of a patient, such that interaction between the one or more targets and the laser pulses is characterized by linear absorption enhanced photodecomposition without formation of a plasma or associated cavitation event; and an exogenous chromophore introduced to the target structure to create/enhance linear absorption. The exogenous chromophore may be trypan blue.

Another embodiment is directed to a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds; and an optical system operatively coupled to the laser source and configured to focus and direct the laser beam in a pattern into one or more intraocular targets within an eye of a patient, such that interaction between the one or more targets and the laser pulses is characterized by linear absorption enhanced photodecomposition without formation of a plasma or associated cavitation event; with the addition of a second laser source configured to fragment the lens utilizing a wavelength between about 800 nm and about 1100 nm. The second laser may be a pulsed infrared laser. The second laser may have a pulse duration between about 1 picosecond and about 100 nanoseconds. The second laser may be a Q-switched Nd:YAG laser.

Other aspects and advantages of the present invention will become apparent from the following detailed description, taken in conjunction with the accompanying drawings, illustrating by way of example the principles of the invention.

BRIEF DESCRIPTION OF THE DRAWINGS

As seen in FIG. 15 in this case no cavitation bubbles will be created. This effect will induce a change of the refractive index profile of the corneal tissue.

DETAILED DESCRIPTION OF ILLUSTRATED EMBODIMENTS

Figure 1:
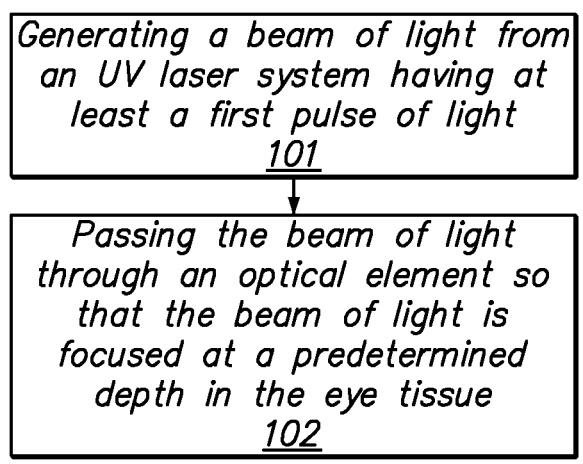
FIG. 1 illustrates a high-level flowchart in accordance with an embodiment of the present invention.

The present invention relates to method and systems for making an incision in eye tissue or alter its mechanical or optical properties. The following description is presented to enable one of ordinary skill in the art to make and use the invention and is provided in the context of a patent application and its requirements. Various modifications to the embodiments and the generic principles and features described herein will be readily apparent to those skilled in the art. Thus, the present invention is not intended to be limited to the embodiment shown but is to be accorded the widest scope consistent with the principles and features described herein.

As shown in the drawings for purposes of illustration, a method and system for making an incision in eye tissue or alter its mechanical or optical properties are disclosed. In varying embodiments, the method and system disclosed herein provide many advantages over the current standard of care. Specifically, rapid and precise openings in the lens capsule are enabled using a 320 nm to 430 nm laser to facilitate the placement and stability of intraocular lenses.

Other procedures enabled by the techniques described herein include the treatment of astigmatism. Intraocular lens (IOLs) are typically used for correcting astigmatism but require precise placement, orientation and stability. Complete and long lasting correction using IOLs is difficult. It often involves further surgical intervention to make the corneal shape more spherical, or at least less radially asymmetrical. This can be accomplished by making Corneal or Limbal Relaxing Incisions. Other procedures include the creation of corneal flaps for LASIK procedure and the creation of matching corneal transplant shapes of the donor and recipient cornea. The present invention may be employed to perform these delicate incisions.

FIG. 1 is a flowchart of a method in accordance with an embodiment. A first step 101 involves generating a beam of light from a 320 nm to 430 nm laser system having at least a first pulse of light. A next step 102 involves passing the beam of light through an optical element so that the beam of light is focused at a predetermined depth in the eye tissue. By implementing this method, rapid and precise openings in the lens capsule are enabled thereby facilitating the placement and stability of intraocular lenses.

Figure 2A:
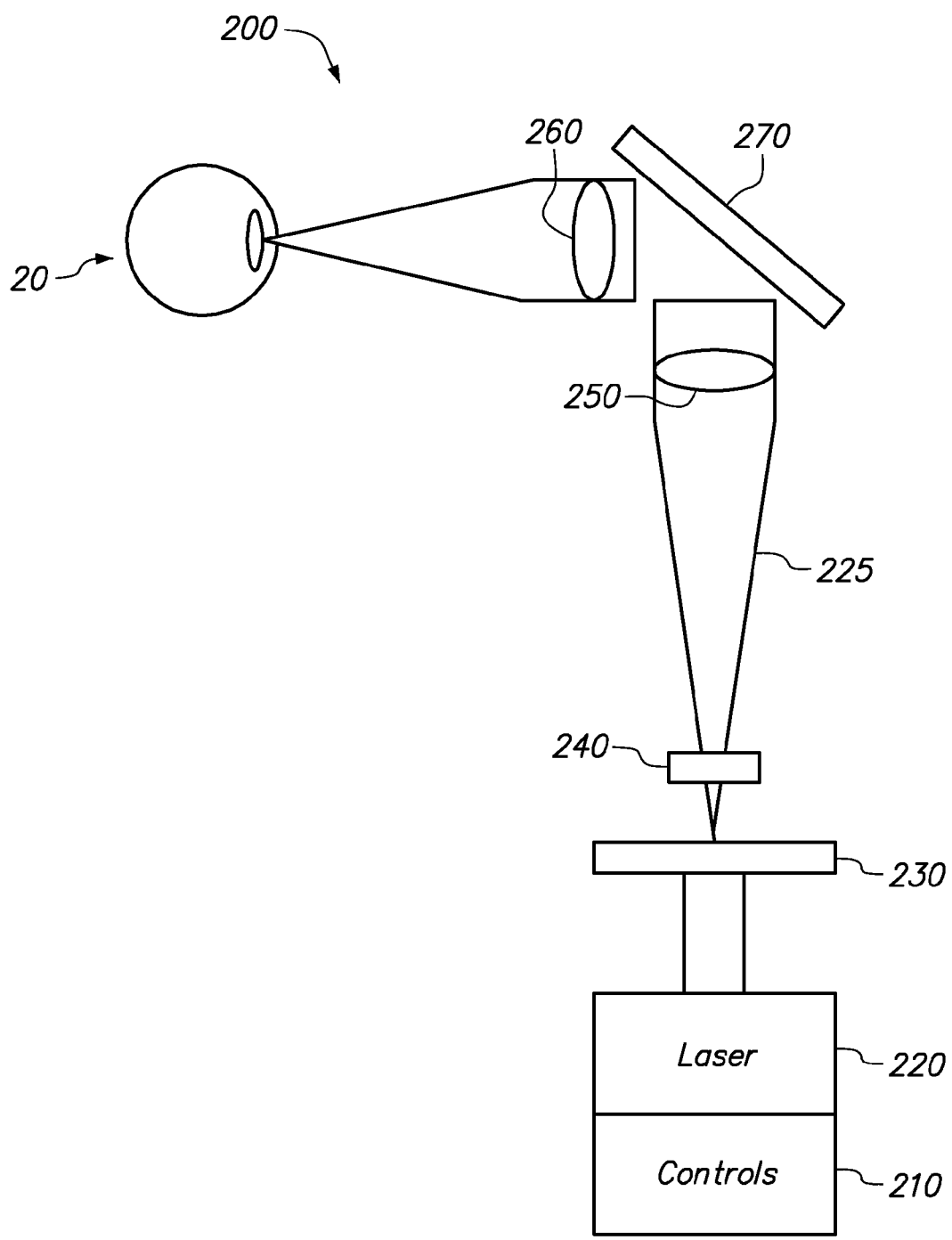
FIGS. 2A & B are illustrations of system embodiments.

The present invention can be implemented by a system 200 that projects or scans an optical beam into a patient's eye 20, such as the system shown in FIG. 2A. The system 200 includes control electronics 210, a light source 220, an attenuator 230, a beam expander 240, focusing lens' 250, 260 and reflection means 270. Control electronics 210 may be a computer, microcontroller, etc. Scanning may be achieved by using one or more moveable optical elements (e.g. lenses 250, 260, reflection means 270) which also may be controlled by control electronics 210, via input and output devices (not shown). Another means of scanning might be enabled by an electro optical deflector device (single axis or dual axis) in the optical path.

During operation, the light source 220 generates an optical beam 225 whereby reflection means 270 may be tilted to deviate the optical beam 225 and direct beam 225 towards the patient's eye 20. Focusing lens' 250, 260 can be used to focus the optical beam 225 into the patient's eye 20. The positioning and character of optical beam 225 and/or the scan pattern it forms on the eye 20 may be further controlled by use of an input device such as a joystick, or any other appropriate user input device.

Figure 14:
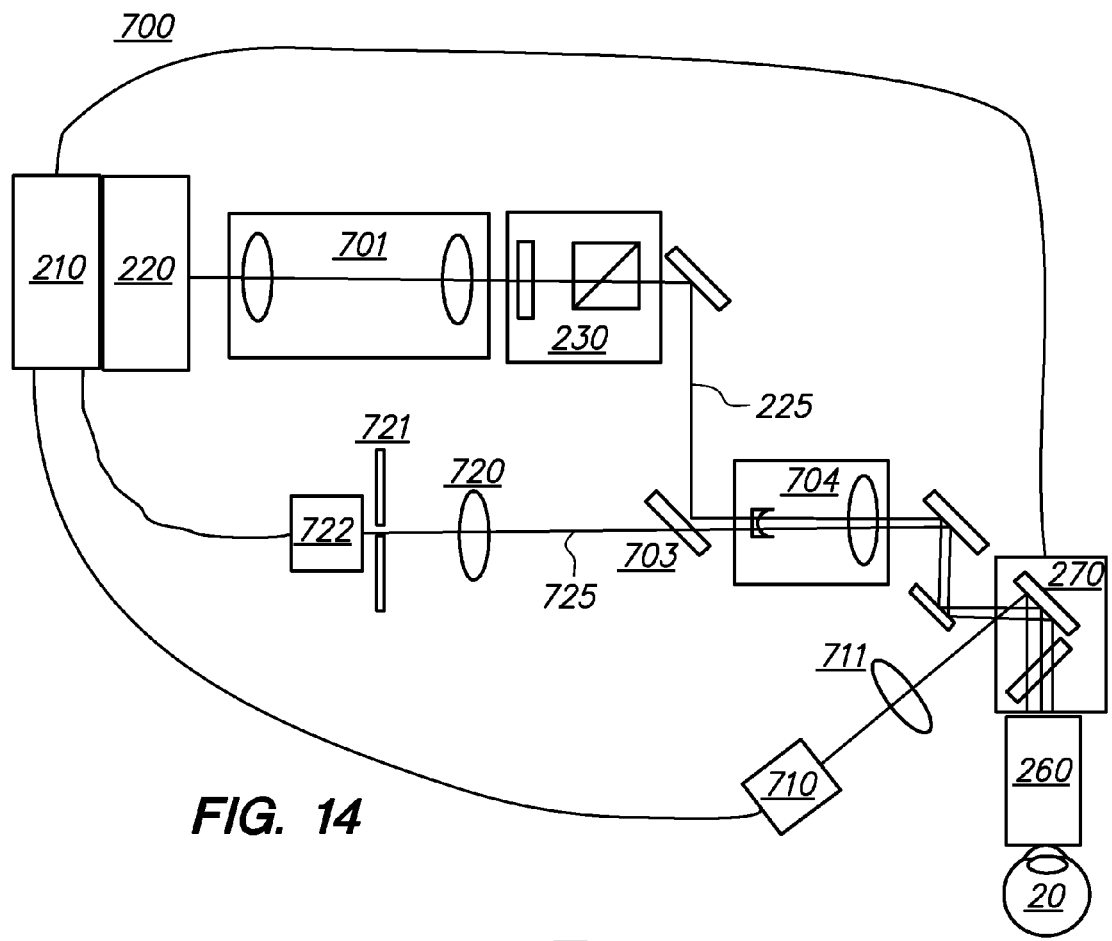
FIG. 14 is another illustration of a system in accordance with an embodiment of this invention.

The present invention alternatively can be implemented by a system 700 that additionally does a range finding of patient's eye 20, such as the system shown in FIG. 14. The system 700 includes control electronics 210, a light source 220, an attenuator 230, a beam expander 701, an optical variable beam attenuator 230, an separate focus lens combination 704 and a beam reflection and scanning means 270. The light beam 225 of light source 220 is focused through focusing lens 260 to its target location 20. This will be controlled by electronics 210 which is connected to deflection unit 270. Additionally the auto fluorescence light 725 of the target structure 20 is de-scanned by the similar optical path shared with laser light 225 by preferred means of a dichroic beam splitter 703 and focused by a lens 720. An aperture pinhole 721 is placed in the focal spot of formed beam 725 as a conjugate of the laser beam (225) focus in target structure 20. The intensity of the transmitted auto fluorescence light through beam aperture 721 is detected and converted to an electrical signal which can be read by the control unit 210. Also an image of the treated area is imaged by lens 711 on an image capture device 710 which can be a CCD or a CMOS camera. Also this signal is transmitted to control unit 210.

In another variation of system 700 the detection combination unit 703, 720, 721, 722 is used to confocally detect the back reflected light of beam 225 from sample 20.

The underlying mechanism of varying embodiment employs a 320 nm to 430 nm laser source. The ultraviolet optical spectrum is technically subdivided into three major spectral regions which are: UVA (400 nm-315 nm), UVB (315 nm-280 nm), UVC (280 nm-100 nm). Due to their high single photon energy, UVB and UVC light is commonly associated with carcinogenic effects due to their ability to directly modify DNA. While water is still transparent down to 200 nm the absorption of proteins strongly increases around 240 nm. This strong protein absorption in the UVC spectral region, which is also the leading absorption in corneal tissue, is clinically used nowadays in Laser-Assisted in situ Keratomileusis (LASIK) procedures to precisely ablate the corneal tissue.

UVC lasers have been used to ablate biological tissue through photodissociation, the absorption of a high energy photon to break bonds within an organic molecule. A list of such common bonds is given in the table below along with their dissociation energies listed in terms of wavelength. The shorter the wavelength, the stronger the bond.

| Bond | Energy nm |
|---|---|
| C—H, sp3 | 292 |
| C—H, sp | 239 |
| C═C | 199 |

From this table it is obvious that highly energetic photons are required for the photodissociation of biological materials, such as is discussed in U.S. Pat. No. 4,784,135 by Blum, et al. This effect is the basis of numerous photo-medical systems, especially in ophthalmology where 193 nm excimer lasers are routinely used for corneal modification. Embodiments of the present invention utilize an altogether different physical phenomenon and different spectral region (UVA to green) to modify and or ablate biological tissue that is neither present nor considered in the prior art.

In an embodiment, the light source 220 is an 320 nm to 430 nm laser source such as an Nd:YAG laser source operating at the $3^{rd}$ harmonic wavelength, 355 nm. The transmission of the cornea at 355 nm is about 85% and starts to strongly drop off at 320 nm (50% transmission) to 300 nm with about 2% transmission whereas the lens absorption is ~99%. Also, for older people, light scattering of the cornea is minimal while light scattering of the lens has considerably increased (cataract).

The effect of light scattering is sensitive to wavelength. In case of scatter centers smaller than the used wavelength, the scattering coefficient scales as $\lambda^{-4}$. For larger scatterers with a size range within the size of the wavelength, the Mie approximation is well suited for describing the scattering function. For particles with sizes between 350 and 700 nm in size, the scattering coefficient scales as $\lambda^{-1}$. The aged lens itself absorbs all wavelengths shorter than 420 nm and is a strong scatterer. This implies that shorter wavelengths can be used for the laser cutting of the anterior part of the aged lens, especially the lens capsule, while serving to protect the retina by effectively attenuating the light ultimately disposed there.

Q-switched infrared lasers with energies of several milliJoule and in the IR spectral range (1064 nm) are routinely employed to treat posterior cataract opacification. They do so by providing a reliable plasma formation directly behind the posterior lens capsule. These pulses create cavitation bubbles of several millimeter in size and peak pressures in the kilobar range. Mechanical effects of the cavitation bubbles with their sizes in the millimeter range are the limiting factor for highly precise cutting in a liquid environment. In order to reduce the bubble size and commensurate mechanical side-effects that yield incisions with poor edge quality and therefore poor mechanical strength, laser pulse energy must be significantly reduced. Such an interaction would, however, be well suited for the application of lens conditioning.

Q-switched green lasers with energies of several milli-Joule and several nanoseconds pulse duration are routinely employed to treat open angle glaucoma of the eye. This therapy named Selective Laser Trabecuplasty (SLT) utilizes the specific targeting of the melanin chromophore naturally present in the trabecular meshwork. The laser itself uses a relatively large 200 micrometer spot size to cover most of the target issue area. The laser produces also a cavitation bubble around the melanin absorber but this effect is due to linear heating than plasma formation as used in the posterior cataract treatment with Q-switched IR laser pulses.

In an embodiment of the invention the use of UV wavelengths, significantly reduces the threshold for plasma formation and associated formation of cavitation bubbles but also decreases the threshold energy required for linear absorption enhanced photodecomposition without the formation of cavitation bubbles for a few reasons. First, the focused spot diameter scales linearly with wavelength which squares the peak radiant exposure within the focal plane. Second, the linear absorption of the material itself allows an even lower threshold for plasma formation or low density photodecomposition as initially more laser energy is absorbed in the target structure. Third, the use of UV laser pulses in the nanosecond and sub-nanosecond regime enables linear absorption enhanced photodecomposition and chromophore guided ionization.

Furthermore, this chromophore guided ionization strongly lowers the threshold for ionization in case of plasma formation as well lowers the threshold for low density photodecomposition for material modification or alteration without cavitation even under very weak absorption. Due to the high fluence densities even minimal linear absorption strongly lowers the threshold for an effect. It has been shown (Colombelli et al., Rev. Sci. Instrum. 2004, Vol 75, pp. 472-478) that the threshold for plasma formation and the generation of cavitation bubbles can be lowered by an order of magnitude if one only changes from high purity water to water with a physiologic NADH concentration of 38 mMol. The linear absorption also allows for the specific treatment of topical lens structures (e.g. the lens capsule) as the optical penetration depth of the laser beam is limited by the linear absorption of the lens. This is especially true for aged lenses which absorption in the UV-blue spectral region increases strongly compared to young lenses.

Additionally in another embodiment of this invention the linear absorption effect on the target structures can be even enhanced by applying exogenouse chromophors. One such useful chromophore is trypan blue which is commonly used in surgery to stain the lens capsule in case of the absence of the fundus red reflex. Trypan blue also has an increased linear absorption at wavelengths shorter than 370 nm. This linear absorption further reduces the energy required to create disclosed effect on the lens capsular surface.

This method can also be used for the alteration of the overall refractive power of the human eye by:
i. Create cuts (incisions) within the cornea to change its shape to alter its refractive power ii. Modify the refractive index of the corneal tissue to induce a change of its effective refractive power.
iii. Modify the refractive index of an implanted synthetic IOL by writing Fresnel lenses or such other similar into the IOL material to change its effective refractive power
iv. Any combination of i, ii, & iii.

The present inventive system enables surgical techniques that include utilizing a pulsed 320 nm to 430 nm laser to perform highly precise physical modifications of ocular targets, including tissues (such as lens, lens capsule, cornea, etc.) and synthetic intraocular lens implants. This can be done in two different operating regimes; with or without cavitation bubble formation. The sub-cavitation regime can also be used to modify the refractive index of ocular targets. Although the wavelengths used in the present invention are shorter or in the range than those associated with retinal blue light toxicity, the absorption of the 320 nm to 400 nm laser light within the aged lens further minimizes the risk of retinal damage, as this light will be absorbed by the lens volume. Furthermore, the risk of damaging the corneal endothelium or other corneal structures is also minimized. The threshold pulse energy will be $E_{th}=\Phi*d^2/4$, where $\Phi$ is the threshold radiant exposure and d is the focal spot diameter. Here, the focal spot diameter, d, is $d=\lambda F/D_b$, where $\lambda$ is the wavelength, F is the focal length of the last focusing element and $D_b$ is the beam diameter of the last lens. For stable and reproducible operation, pulse energy should exceed the threshold by at least a factor of 2, however, the energy level can be adjusted to avoid damage to the corneal endothelium.

In varying embodiments, the 320 nm to 430 nm laser provides pulse energies of between 0.01 µJ and 500 µJ, preferably between 0.1 µJ to 10 µJ, a repetition rate of 500 Hz up to 500 kHz with a pulse duration of between 1 ps and 100 ns, preferably 400 ps. Laser spot sizes smaller than 10 um, typically 3 um to 0.5 um are used. However, one of ordinary skill in the art will readily recognize that a variety of parameters could be employed while remaining within the spirit and scope of the present inventive concepts.

Figure 10:
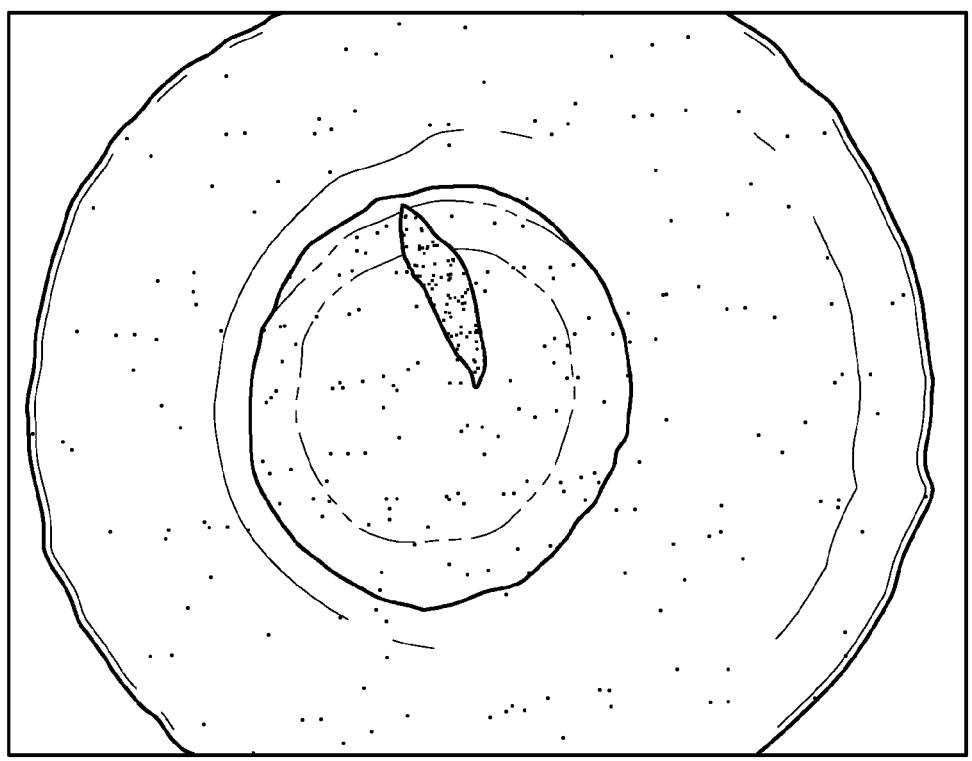
FIG. 10 illustrates fragmentation patterns of an ocular lens produced by one embodiment of the present invention.
Figure 11:
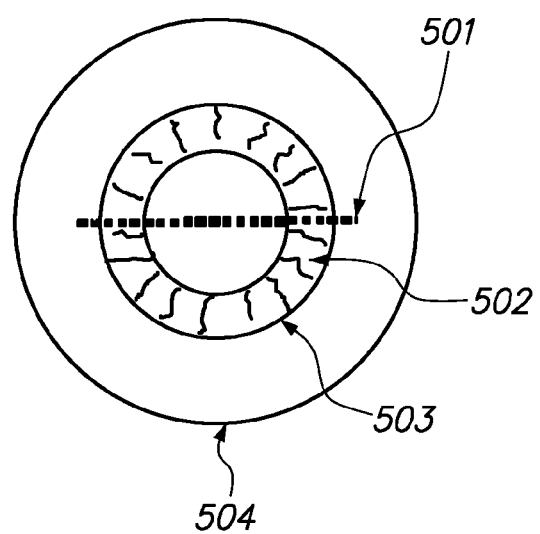
FIG. 11 illustrates a line pattern 501 applied across the cornea 504 and lens for depth ranging measurement (OCT, confocal reflection, confocal autofluorescence, ultrasound) of the axial profile of the anterior chamber of the eye. It goes over the iris 502 and the lens 402 (not shown)
Figure 12:
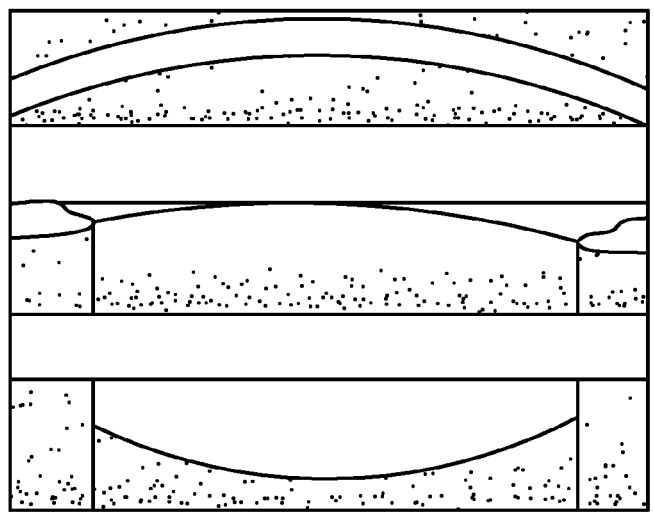
FIG. 12 illustrates a measured scan pattern across the cornea and lens which can be used for depth ranging by OCT
Figure 13:
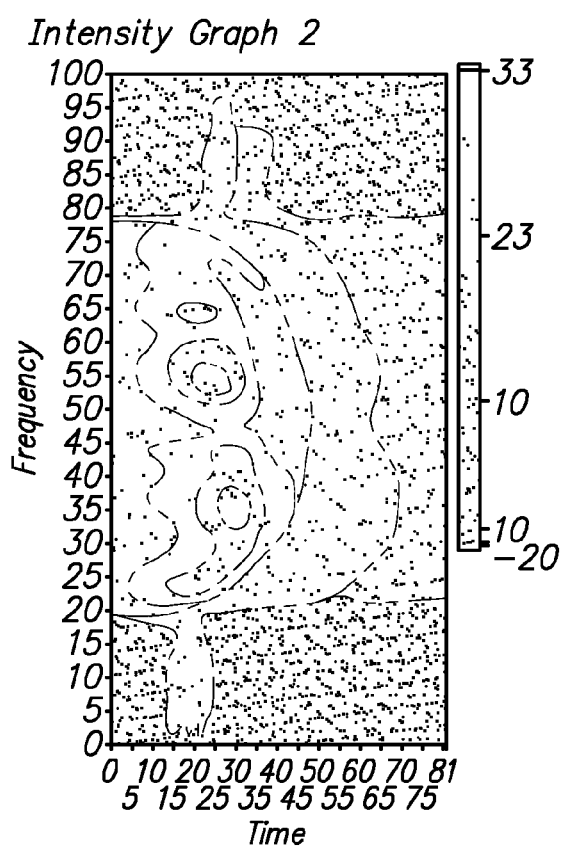
FIG. 13 illustrates a measured scan pattern across the lens which can be used for depth ranging by confocal autofluorescence using a pulsed 320 NM TO 430 NM laser.

An example of the results of such a system on an actual human crystalline lens is shown in FIG. 10. A beam of 4 µJ, 400 ps pulses delivered at a pulse repetition rate of 0.5 kHz from a laser operating at a wavelength of 355 nm was focused at NA=0.15, using an irradiance of about 120 gigaWatts per square centimeter. This produced the capsulotomy patterns in the human lens shown in FIG. 10. In this case no cavitation bubbles were formed to induce the cuts. This was confirmed visually under the microscope but also by using a hydrophone for the detection of the acoustic sound wave emitted by cavitation bubbles. For laser cataract surgery, the only high precision cut on the lens itself is the capsulotomy. For the softening or fragmentation of the lens nucleus, the patterns don't need a high spatial confinement. So for this application even if there is a longer pulse, a higher fluence and/or irradiance threshold is acceptable.

Figure 3:
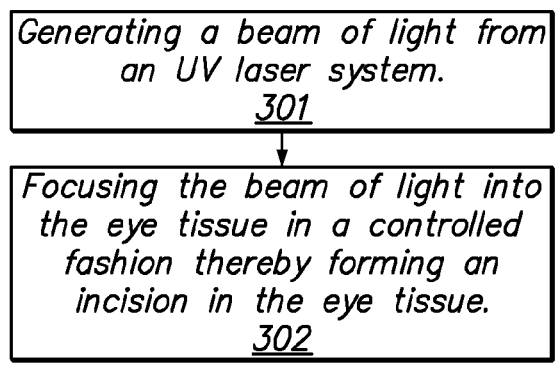
FIG. 3 shows a flowchart of a method in accordance with an alternate embodiment.

FIG. 3 shows a flowchart of a method in accordance with an alternate embodiment. A first step 301 involves generating a beam of light from a 320 nm to 430 nm laser system. A next step 302 involves translating the focused beam of light within the eye tissue in a controlled fashion thereby forming an incision. In an embodiment, the incision is formed in the anterior lens capsule of the eye tissue in the performance of a capsulorhexis. Alternately, the incision may be in the cornea for the purposes of astigmatic correct or creating surgical access. For example, clear corneal cataract instrumentation and paracentesis incisions maybe used to provide surgical access.

The control electronics 210 and the lights source 220 can be set to target the surfaces of the targeted structures in the eye 20 and ensure that the beam 225 will be focused where appropriate and not unintentionally damage non-targeted tissue. Imaging modalities and techniques described herein, such as for example, Optical Coherence Tomography (OCT), Purkinje imaging, Scheimpflug imaging, autofluorescence imaging, confocal autofluorescence, confocal reflectance imaging or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, OCT, Purkinje imaging, Scheimpflug imaging, structured light illumination, ultrasound, or other known ophthalmic or medical imaging modalities and/or combinations thereof. It should be noted that the imaging depth need only include the anterior most portion of the intraocular target, and not necessarily the entire eye or even the anterior chamber.

Additionally confocal reflectometry can be used for the adjustment of delivered laser energy during treatment as it will be able to detect if a cavitation bubble is formed after a laser pulse and adjust the energy of subsequent laser pulses or monitor the laser induced change of the refractive index of said tissue.

Accordingly, a three dimensional application of laser energy can be applied across the capsule along the pattern produced by the laser-induced effect in a number of ways. For example, the laser can be employed to produce several circular or other pattern scans consecutively at different depths with a step equal to the axial length of the effect zone. Thus, the depth of the focal point (waist) in the tissue is stepped up or down with each consecutive scan. The laser pulses are sequentially applied to the same lateral pattern at different depths of tissue using, for example, axial scanning of the focusing elements or adjusting the optical power of the focusing element while, optionally, simultaneously or sequentially scanning the lateral pattern.

The adverse result of laser beam scattering on bubbles, cracks and/or tissue fragments prior to reaching the focal point can be avoided by first producing the pattern/focusing on the maximal required depth in tissue and then, in later passes, focusing on more shallow tissue spaces. Not only does this "bottom up" treatment technique reduce unwanted beam attenuation in tissue above the target tissue layer, but it also helps protect tissue underneath the target tissue layer. By scattering the laser radiation transmitted beyond the focal point on gas bubbles, cracks and/or tissue fragments which were produced by the previous scans, these defects help protect the underlying retina. Similarly, when segmenting a lens, the laser can be focused on the most posterior portion of the lens and then moved more anteriorly as the procedure continues.

Figure 2B:
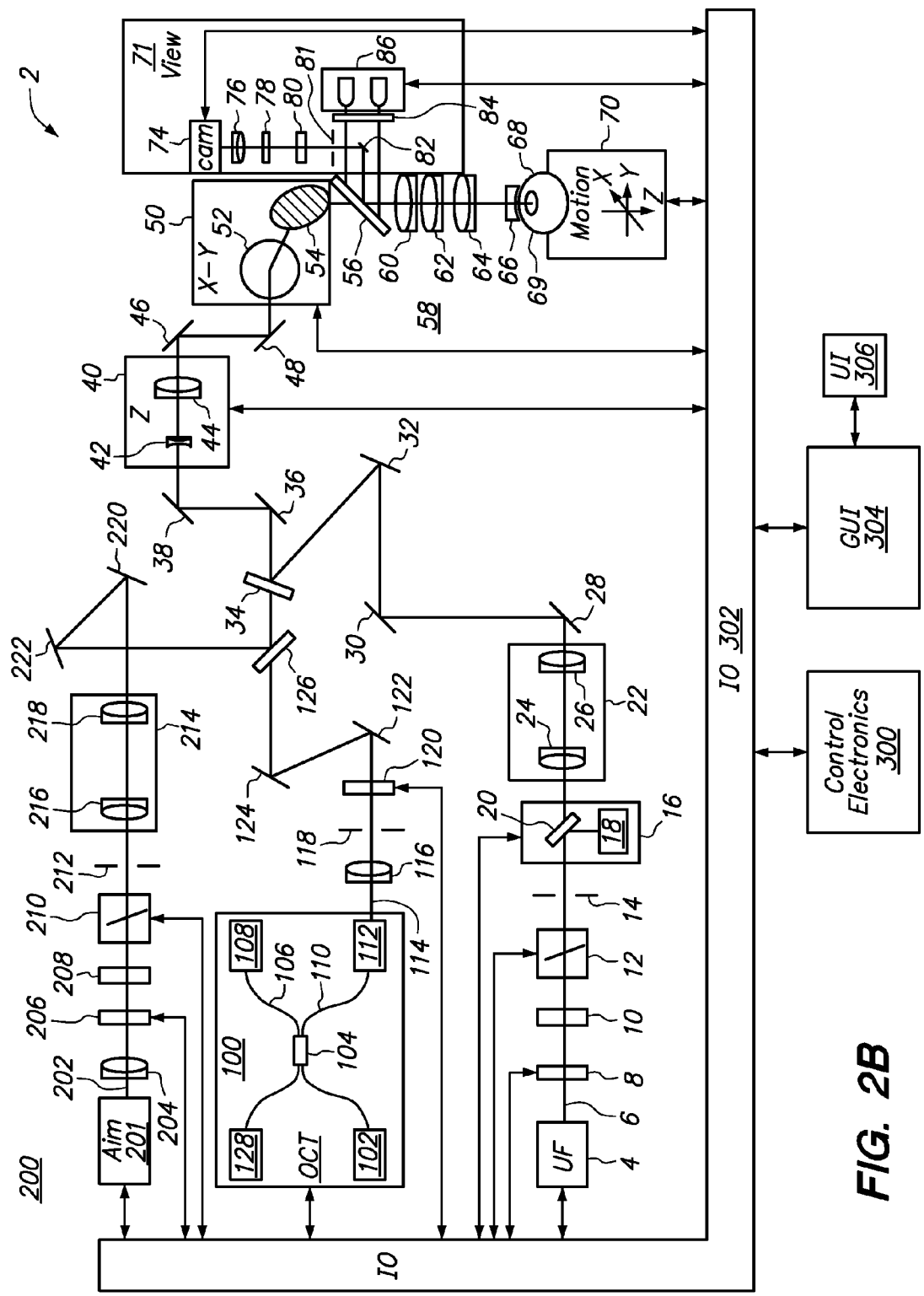

The present invention can be implemented by a system that projects or scans an optical beam into a patient's eye 68, such as system 2 shown in FIG. 2B which includes a TREATMENT light source 4 (e.g. a short pulsed 355 nm laser). Using this system, a beam may be scanned in a patient's eye in three dimensions: X, Y, Z. Safety limits with regard to unintended damage to non-targeted tissue bound the upper limit with regard to repetition rate and pulse energy; while threshold energy, time to complete the procedure and stability bound the lower limit for pulse energy and repetition rate.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated TREATMENT light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the TREATMENT beam 6. Additionally, the orientation of linear polarizer 10 determines the incident polarization state incident upon beamcombiner 34, thereby optimizing beamcombiner throughput.

The TREATMENT beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the TREATMENT beam 6 (and transmits both the OCT 114 and aim 202 beams described below). For efficient beamcombiner operation, the angle of incidence is preferably kept below 45 degrees and the polarization where possible of the beams is fixed. For the TREATMENT beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of TREATMENT focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An objective lens 58 of focal length 60 mm, operating over a field of 7 mm, with an input beam size of 20 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The TREATMENT laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, structured light illumination, confocal backreflectance imaging, fluorescence imaging, or ultrasound may be used to determine the location and measure the thickness of the lens and lens capsule to provide greater precision to the laser focusing methods, including 2D and 3D patterning, or other known ophthalmic or medical imaging modalities and/or combinations thereof. In the embodiment of FIG. 2A, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information is then be loaded into the control electronics 300, and used to program and control the subsequent laser-assisted surgical procedure. The information may also be used to determine a wide variety of parameters related to the procedure such as, for example, the upper and lower axial limits of the focal planes used for modifying the lens capsule, cornea, and synthetic intraocular lens implant, among others.

The OCT device 100 in FIG. 2A includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the TREATMENT laser system. The return signals from both the reference and sample arms 106, 110 are then directed by coupler 104 to a detection device 128, which employs one of the following; time domain, frequency domain, or single point detection techniques. In FIG. 2A, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the TREATMENT beam 6 in the focal plane and therefore the OCT beam 114 is smaller in diameter than the TREATMENT beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to TREATMENT beam 6 subsequent to beamcombiner 34. Similarly, beamcombiner 126 is used to combine the OCT beam 114 with the aim beam 202 described below.

Once combined with the TREATMENT beam 6 subsequent to beamcombiner 34, OCT beam 114 follows the same path as TREATMENT beam 6 through the rest of the system. In this way, OCT beam 114 is indicative of the location of TREATMENT beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of TREATMENT beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference arm 106. In the case of OCT system 100 used in FIG. 2A, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the TREATMENT focus device due to influences such as immersion index, refraction, and aberration, both chromatic and monochromatic, care must be taken in analyzing the OCT signal with respect to the TREATMENT beam focal location. A calibration or registration procedure as a function of X, Y Z should be conducted in order to match the OCT signal information to the TREATMENT focus location and also to the relate to absolute dimensional quantities.

Observation of an aim beam may also be used to assist the user to directing the TREATMENT laser focus. Additionally, an aim beam visible to the unaided eye in lieu of the infrared OCT and TREATMENT beams can be helpful with alignment provided the aim beam accurately represents the infrared beam parameters. An aim subsystem 200 is employed in the configuration shown in FIG. 2A. The aim beam 202 is generated by an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

It should be also noted that TREATMENT beam may also be attenuated to the nanoJoule level and used instead of the OCT system described above. Such a configuration provides for the most direct correlation between the position of the focal locations for imaging and treatment—they are the same beam. This attenuated probe beam can be used directly in a backreflectance measuring configuration, or even indirectly in a fluorescence detection scheme. Since you will see increases in both backscatter and fluorescence within tissue structures, both approaches have merit. They may also be utilized to deliver a sparse pattern in order to limit the patient's exposure, while still discerning a reasonable map of the intraocular targets.

Furthermore, since the requisite precision and inclusion size are much more relaxed for lens conditioning as compared to the incision of cornea and lens capsule, the present invention contemplates the addition of a short pulsed IR laser source to the above described system for lens treatments, as was mentioned above in the discussion of the use of milliJoule pulse from Q-switched Nd:YAG lasers for the treatment of posterior opacification. Such pulse energies will cause larger inclusions, which unsuitable for capsular and corneal incisions could provide for robust separation of a cataractous lens. The NIR wavelength is not strongly absorbed or scattered by the lens, as opposed to shorter wavelengths. This second treatment source may have its beam combined with that of the first treatment beam by means of another beam splitter. The large difference in wavelength makes this a fairly straightforward design. However, that same spectral difference will require a different registration to the imaging and/or ranging modality, as was discussed above with respect to FIG. 2B.

Figure 4:
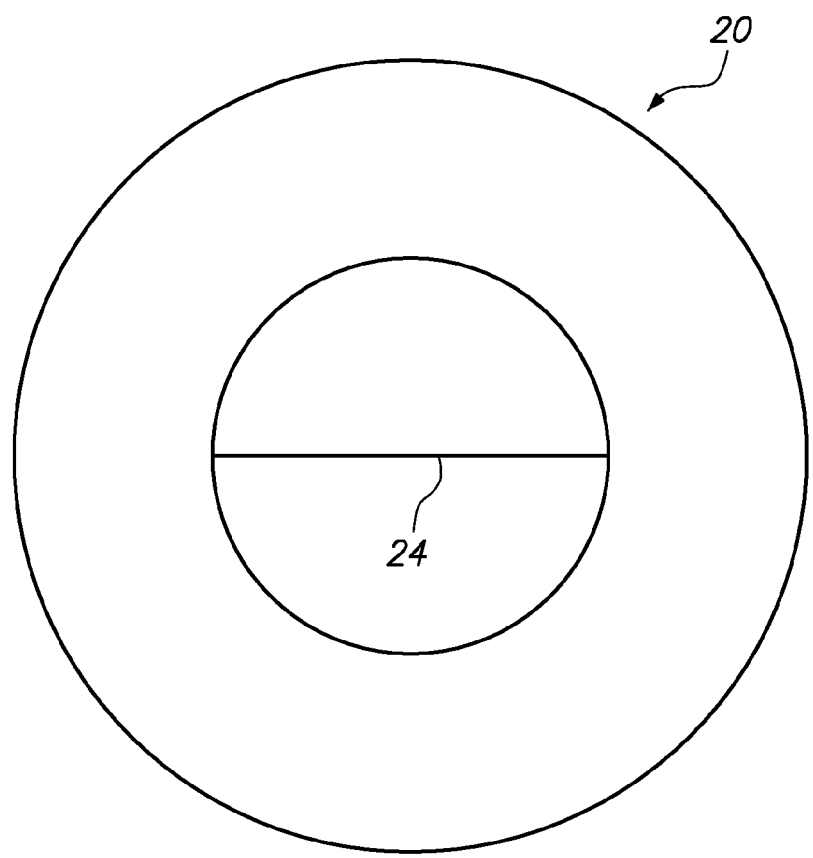
FIG. 4 is an illustration of the line pattern applied across the lens for depth ranging measurement (OCT, confocal reflection, confocal autofluorescence, ultrasound) of the axial profile of the anterior chamber of the eye.

FIG. 4 is an illustration of the line pattern applied across the lens for OCT measurement of the axial profile of the anterior chamber of the eye 20. OCT imaging of the anterior chamber of the eye 20 can be performed along a simple linear scan across the lens using the same laser and/or the same scanner used to produce the patterns for cutting. This scan will provide information about the axial location of the anterior and posterior lens capsule, the boundaries of the cataract nucleus, as well as the depth of the anterior chamber. This information may then be loaded into the laser scanning system, and used to program and control the subsequent laser assisted surgical procedure. The information may be used to determine a wide variety of parameters related to the procedure such as, for example, the upper and lower axial limits of the focal planes for cutting the lens capsule and segmentation of the lens cortex and nucleus, the thickness of the lens capsule among others.

Figure 5:
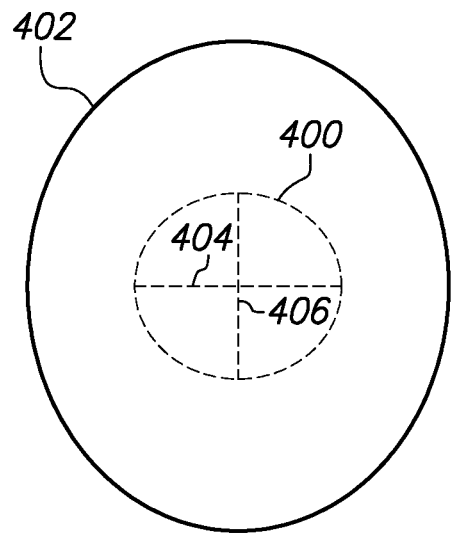
FIG. 5 is a top view diagram of a rotationally asymmetric capsulorhexis incision.

FIGS. 5 through 9 illustrate different aspects of an embodiment of the present invention, which can be implemented using the system 200 described above. As shown in FIG. 5, a capsulorhexis incision 400 (which may be created using system 200) is tailored for astigmatism-correcting intraocular lenses (IOLs). Such astigmatism-correcting IOLs need to be placed not only at the correct location within the capsule 402 of the eye 20, but also oriented at the correct rotational/clocking angle. Thus, they have inherent rotational asymmetries, unlike spherical IOLs. The incision 400 shown in this example is elliptical; however, other shapes are also useful. Incision 400 may be made continuously, or piecewise to largely maintain the structural integrity of the lens-capsule apparatus of the patient's eye 20.

Such incomplete incisions 400 may be thought of as perforated incisions, and may be made to be removed gently in order to minimize their potential to inadvertently extend the capsulorhexis. Either way, incision 400 is an enclosed incision, which for the purposes of this disclosure means that it starts and ends at the same location and encircles a certain amount of tissue therein. The simplest example of an enclosed incision is a circular incision, where a round piece of tissue is encircled by the incision. It follows therefore that an enclosed treatment pattern (i.e. generated by system 200 for forming an enclosed incision) is one that also starts and ends at the same location and defines a space encircled thereby.

One key feature of the enclosed incision 400 is that it includes a registration feature to orient the IOL that will be placed inside it. For the illustrated elliptical incision 400, it elliptical shape is it's registration feature, which allows for the accurate placement of an IOL by virtue of its inherent rotational asymmetry, unlike the desired circular outcome of a manual CCC. The elliptical major axis 404 and minor axis 406 of incision 400 are shown. Major axis 404 and minor axis 406 are not equal. Incision 400 may be made at any rotational angle relative to the eye 20 of a patient, although it is shown in this example to be in the plane of the iris with its major axis 404 lying along the horizontal. Incision 400 is intended to mate with one or more complementary registration features on an IOL. The system 200 may be used to precisely define the surface of the capsule 402 to be incised. This may serve to isolate the laser pulses nominally to the vicinity of the targeted capsule 402 itself, thus minimizing the energy required and the treatment time and commensurately increasing patient safety and overall efficiency.

Figure 6:
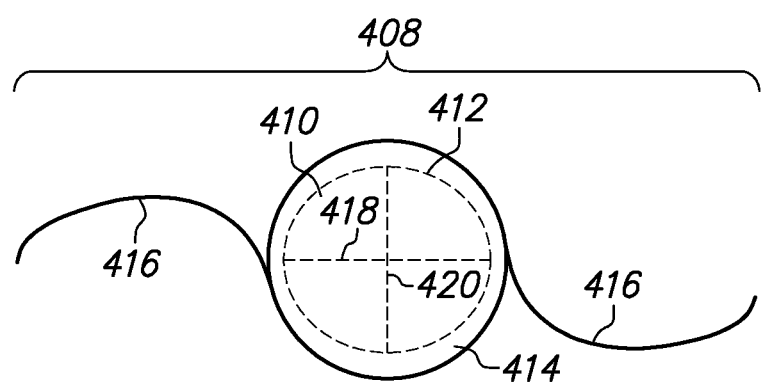
FIG. 6 is a top view diagram of a complementary rotationally asymmetric IOL.

As shown in FIG. 6, an IOL 408 includes an optic portion 410 used to focus light and a haptic 416 used to position the IOL 408. Optic 410 is a rotationally asymmetric lens (about its optical axis) that include an elliptically shaped peripheral sidewall or edge 412, the complementary registration feature that mates with elliptically shaped incision 400. In this example, the elliptically shaped edge 412 includes a major axis 418 and minor axis 420. Major axis 418 and minor axis 420 are not equal. IOL 408 further contains surface 414 that serves to hold haptics element 416 and provide a resting place for capsule 402 to secure optic 410 of intraocular lens 408 in the proper orientation and position within the capsule 402 of a patient's eye 20. Surface 414 is shown as elliptical, but need not be.

Haptics 416 provide stability and may serve to seat edge 412 of intraocular lens 408 in incision 400 by applying retaining force towards the anterior portion of capsule 402. Haptics 416 may be deployed in any orientation. The orientation of the cylindrical correction of optic 410 of intraocular lens 408 may be made to coincide with either its major axis 418 or its minor axis 420. In this way, intraocular lenses IOL 408 and optic 410 may be manufactured in a standardized manner and the rotational orientation of incision 400 and the spherical and cylindrical optical powers of optic 410 may be made to vary to suit the individual optical prescription of the eye 20 of a patient.

Figure 7:
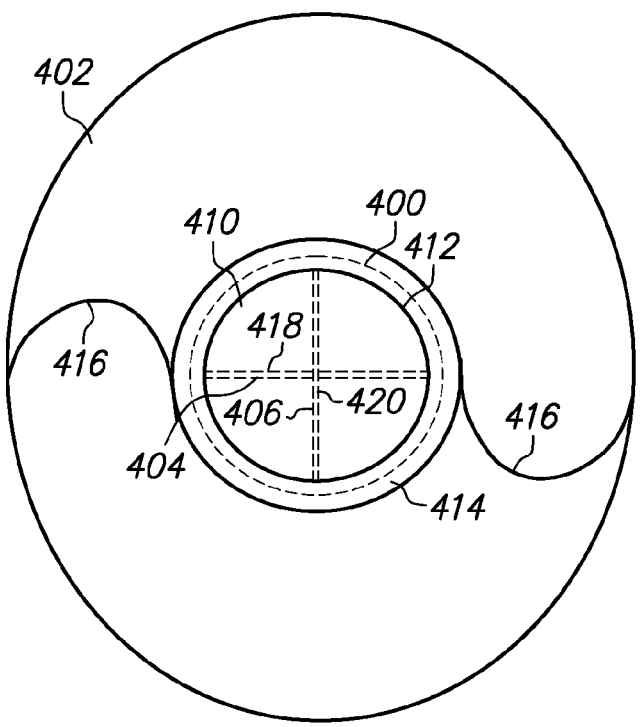
FIG. 7 is a top view the IOL of FIG. 6 positioned in the lens capsule of FIG. 5.

FIG. 7 shows the proper immediate disposition of intraocular lens 408 once installed into capsule 402 with mating registration features edge 412 and incision 400 engaged, and resting upon surface 414. Major axis 404 and major axis 418 are not of equal length. Minor axis 406 and minor axis 420 are not the same length, either. This is done to accommodate the fact the capsule 402 may contract somewhat subsequent to capsulorhexis incision. The difference between the lengths of these axes is intended to allow the capsule 402 to contract and still better seat intraocular lens 408 into capsule 402 via incision 400. These differences should be limited to allow for reasonable contraction, but not so much as to allow for significant rotation of intraocular lens 408. Typical values for these length differences may range from 100 μm to 500 μm, for example.

Figure 8:
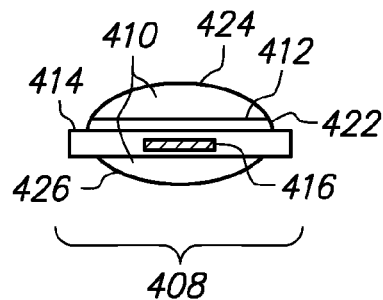
FIGS. 8 and 9 are side views of the rotationally asymmetric IOL of FIG. 6.

FIG. 8 shows a side view on the same intraocular lens 408 depicted in FIGS. 6 and 7. In this schematic representation, edge 412 is shown on the same side of optic 410 as surface 424 of intraocular lens 408. The surface 422 on intraocular lens 408 serves to maintain the integrity of fit between edge 412 and incision 400. Edge 412 is seen as the projection of surface 422 in the alternate view depicted in FIGS. 6 and 7. Optical axis 411 of optic 410 is shown. Haptics 416 lie along the line of sight in this view.

Figure 9:
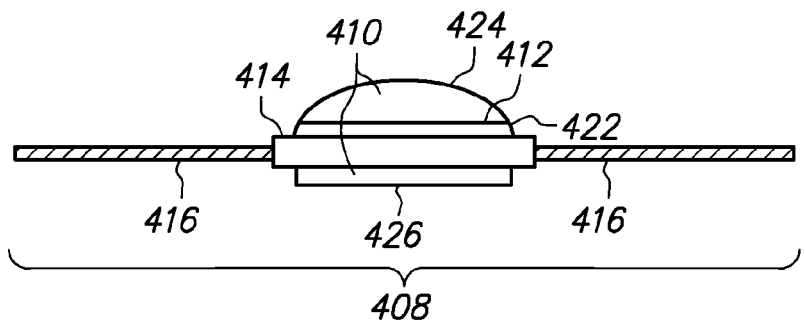

FIG. 9 is a side view of the lens configuration of FIG. 8, but rotated 90 degrees to show that displaying surface 426 is not curved in both directions (i.e. shaped as a cylindrical lens). This cylindrical or toric optical system of optic 410 provides cylindrical correction for the astigmatism of a patient. Haptics 416 lie perpendicular to the line of sight in this view.

Figure 15:
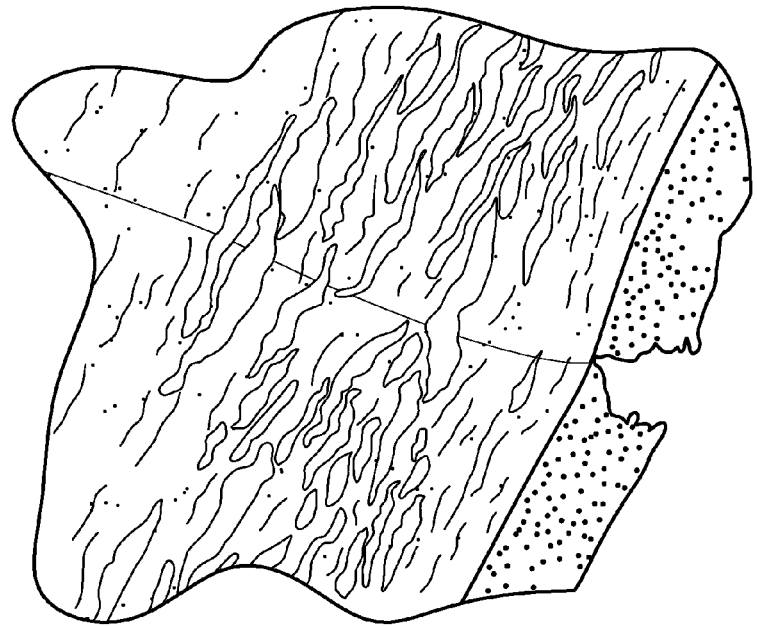
FIG. 15 shows a histological cross section of a corneal cut produced by one embodiment of the present invention in which no cavitation bubbles were formed but the tissue was modified.
Figure 16:
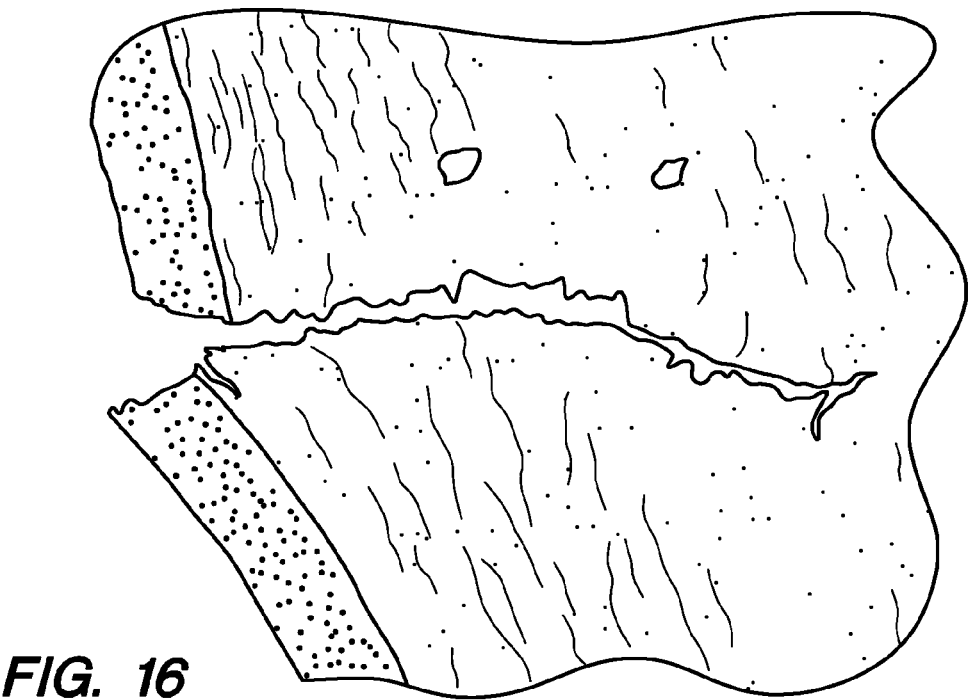
FIG. 16 shows a histological cross section of a opened corneal cut which was produced by one embodiment of the present invention in which no cavitation bubbles were formed as shown in FIG. 15. The cut opened up effortless along the modified tissue structure.
Figure 17:
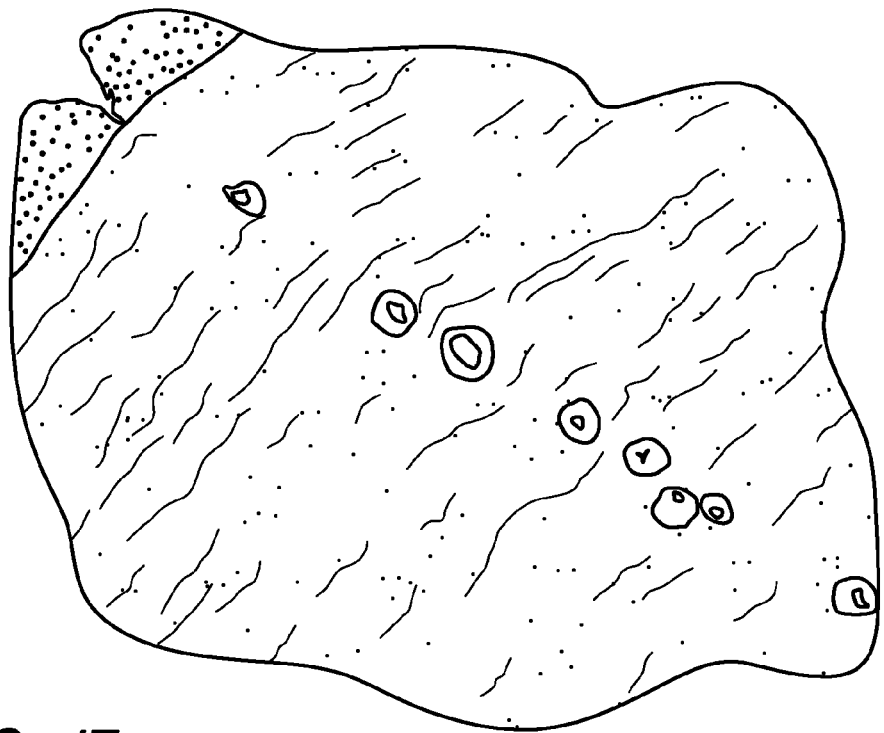
FIG. 17 shows a histological cross section of a corneal cut produced by one embodiment of the present invention in which cavitation bubbles were formed.
Figure 18:
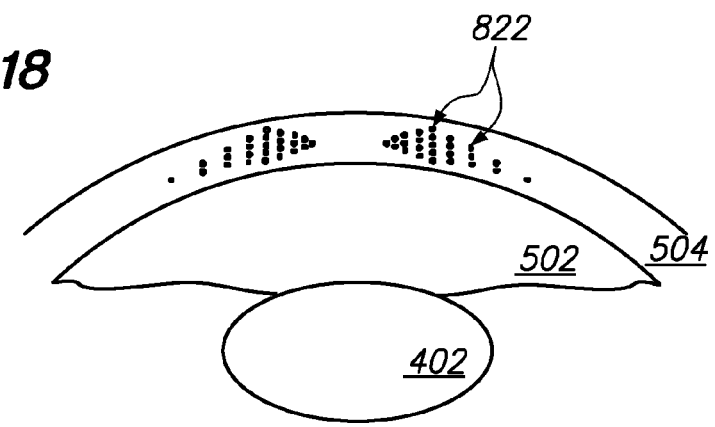
FIG. 18 shows an illustration of the refractive index changes 822 locally induced to the corneal tissue 504 by said invention.
Figure 19:
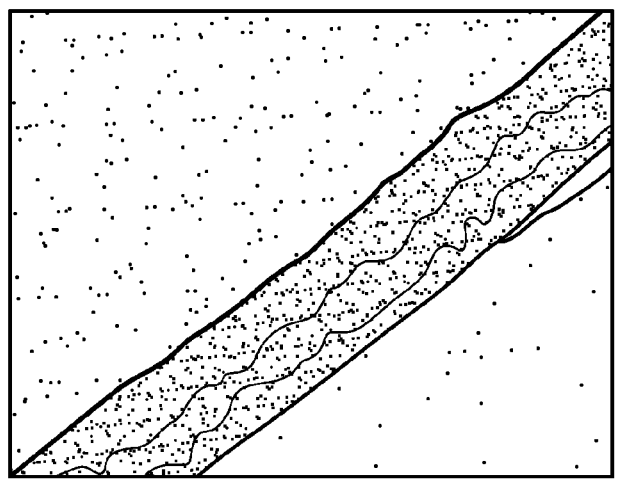
FIG. 19 shows a high resolution SEM image of the excised human lens capsule processed with the current invention. Compared to FIG. 20 this sample has a much smoother edge quality and does not show any effect of cavitation bubbles.
Figure 20:
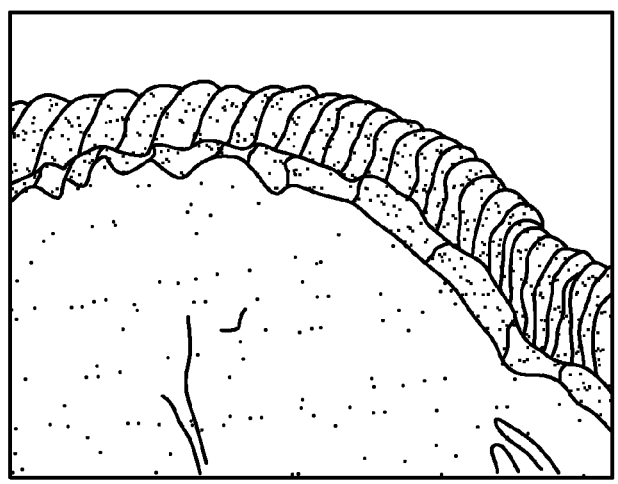
FIG. 20 shows a high resolution SEM image of an excised human lens capsule processed with a femtosecond laser. The effect of each single laser shot with spacing of 5 micrometer is visible as the mechanical effect of cavitation causes the rupture of the capsular tissue.

As shown in FIG. 15 the system can also be used to alter the structure of for example corneal tissue without generating a cavitation bubble as shown in FIG. 16. These alterations of the corneal tissue can be used to shape the refractive index profile of the cornea 504 itself as illustrated in FIG. 18. A multitude of small localized modifications 822 can be induced within the cornea which will change the refractive profile by altering the refractive index itself but also the mechanical strength of corneal tissue. So not only a change of index but also a change of corneal topography can be used. This is achieved by tightly controlling the lateral spacing of the laser effects utilizing beam deflection units 270 and focus shifting unit 704 through focusing unit 260.

As shown in the drawings for purposes of illustration, a method and system for making physical modifications (structural alterations) or incisions in eye tissue has been disclosed. In varying embodiments, the method and system disclosed herein provide many advantages over the current standard of care. Specifically, rapid and precise openings in the lens capsule are enabled using a 320 nm to 430 nm laser to facilitate the placement and stability of intraocular lenses. But also the alteration of the refractive power of the corneal tissue by locally altering the refractive index and reshaping the corneal topography.

Without further analysis, the foregoing so fully reveals the gist of the present inventive concepts that others can, by applying current knowledge, readily adapt it for various applications without omitting features that, from the standpoint of prior art, fairly constitute essential characteristics of the generic or specific aspects of this invention. Therefore, such applications should and are intended to be comprehended within the meaning and range of equivalents of the following claims. Although this invention has been described in terms of certain embodiments, other embodiments that are apparent to those of ordinary skill in the art are also within the scope of this invention.

The invention claimed is:

1. A system for ophthalmic surgery of an eye of a patient, comprising:
a laser source, under the operative control of a controller, configured to alternatively deliver an ultraviolet treatment laser beam and an ultraviolet probe laser beam, each laser beam comprising a plurality of ultraviolet laser pulses having a wavelength between 320 nanometers and 370 nanometers, the ultraviolet treatment laser beam having a pulse duration between 400 picoseconds and 700 picoseconds, and a pulse energy between 0.01 microJoules and 500 microJoules, wherein a pulse energy of the ultraviolet probe laser beam is lower than the pulse energy of the ultraviolet treatment laser beam;
an optical system operatively coupled to the laser source by the controller, the optical system having a numerical aperture of 0.15 and a scan range of 6 mm to 10 mm in a direction lateral to a Z-axis aligned with the laser beam; and
an imaging system operatively coupled to the laser source and optical system by the controller,
wherein the controller is programmed to operate the laser source, the optical system and imaging system to:
focus the ultraviolet treatment laser beam to a focal spot and direct the focal spot in a pattern into the one or more intraocular targets selected from the group consisting of a cornea, a limbus, a sclera, a lens capsule, a crystalline lens, and a synthetic intraocular lens implant; and direct the ultraviolet probe laser beam to the at least one or more intraocular targets and to confocally detect back reflected light of the probe laser beam from the at least one or more intraocular targets, thereby obtaining image data corresponding to the one or more intraocular targets, wherein the pattern creates one or more cuts in the one or more intraocular targets selected from the group consisting of one or more corneal relaxing incisions, one or more limbal relaxing incisions, one or more astigmatic keratotomies, one or more corneal flaps, one or more corneal transplant shapes, and one or more capsulotomies.

2. The system of claim 1, wherein the wavelength is 355 nm.

3. The system of claim 1, wherein the pulse energy is between 0.5 microJoules and 10 microJoules.

4. The system of claim 1, wherein the plurality of laser pulses have a repetition rate of between 500 Hertz and 500 kiloHertz.

5. The system of claim 1, wherein the diameter of the focal spot is between 0.5 microns and 10 microns within the one or more intraocular targets.

6. The system of claim 1, wherein an index of refraction of the modified target is changed.

7. The system of claim 1, wherein an irradiance of the ultraviolet treatment laser beam is less than or equal to 120 gigawatts per square centimeter.

8. The system of claim 1, wherein the imaging system is configured to (1) locate the target structure and (2) monitor for the occurrence of a cavitation event associated with formation of plasma, wherein detection of a cavitation event results in reduction of pulse energy of subsequent laser pulses in order to avoid cavitation.

9. The system of claim 1, wherein the pattern comprises a segment in the Z-axis that is aligned with the treatment laser beam, and the optical system comprises an X-Y scan device and a Z-scan device, the Z-scan device being operable to automatically move the focal spot along the segment in the z-axis that is aligned with the treatment laser beam, the X-Y scan device being operable to move the focal spot laterally to the z-axis, and wherein the treatment laser beam propagates through the Z-scan device prior to propagating to the X-Y scan device.

10. The system of claim 1, further comprising wherein the controller automatically generates the treatment scan pattern based at least in part on the image data.

11. A system for ophthalmic surgery of an eye of a patient, comprising:

a laser source, under the operative control of a controller, configured to alternatively deliver an ultraviolet treatment laser beam and an ultraviolet probe laser beam, each laser beam comprising a plurality of ultraviolet laser pulses having a wavelength between 320 nm and 400 nm, a pulse duration between 400 picoseconds and 700 picoseconds, and a pulse energy, wherein the pulse energy of the ultraviolet probe laser beam is lower than the pulse energy of the ultraviolet treatment laser beam;

an optical system operatively coupled to the laser source by the controller, the optical system having a numerical aperture of 0.15 and a scan range of 6 mm to 10 mm in a direction lateral to a Z-axis aligned with the laser beam; and an imaging system operatively coupled to the laser source and optical system by the controller, wherein the controller is to operate the laser source, the optical system and imaging system to:

focus the ultraviolet treatment laser beam to a focal spot and direct the focal spot in a treatment scan pattern into the one or more intraocular targets selected from the group consisting of a cornea, a limbus, a sclera, a lens capsule, a crystalline lens, and a synthetic intraocular lens implant; and direct the ultraviolet probe laser beam to the at least one or more intraocular targets and to confocally detect back reflected light of the ultraviolet probe laser beam from the at least one or more intraocular targets, thereby obtaining image data corresponding to the one or more intraocular targets, wherein the treatment scan pattern creates one or more cuts in the one or more intraocular targets selected from the group consisting of one or more corneal relaxing incisions, one or more limbal relaxing incisions, one or more astigmatic keratotomies, one or more corneal flaps, one or more corneal transplant shapes, and one or more capsulotomies.

12. The system of claim 11, further comprising a second laser source configured to fragment the lens with a wavelength between 800 nanometers and 1100 nanometers.

13. The system of claim 11, wherein the imaging system is configured to locate the intraocular target.

14. The system of claim 11, wherein the controller automatically generates the treatment scan pattern based at least in part on the image data.

15. The system of claim 11, wherein the pulse energy of the laser pulses is between 0.01 microJoules and 500 microJoules.

* * * * *